United States Patent
Baldwin et al.

(10) Patent No.: US 7,820,411 B2
(45) Date of Patent: Oct. 26, 2010

(54) ESCHERICHIA COLI-DERIVED VACCINE AND THERAPY AGAINST BOTULISM

(75) Inventors: Michael Baldwin, Milwaukee, WI (US); Marite Bradshaw, Madison, WI (US); William H. Tepp, Stoughton, WI (US); Eric A. Johnson, Madison, WI (US); Joseph T. Barbieri, Milwaukee, WI (US); Christina L. Pier, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 45 days.

(21) Appl. No.: 12/040,542

(22) Filed: Feb. 29, 2008

(65) Prior Publication Data

US 2009/0017495 A1 Jan. 15, 2009

Related U.S. Application Data

(62) Division of application No. 11/289,851, filed on Nov. 30, 2005, now abandoned.

(60) Provisional application No. 60/632,502, filed on Dec. 2, 2004.

(51) Int. Cl.
*C12P 21/02* (2006.01)

(52) U.S. Cl. .................................... 435/71.3; 435/69.1

(58) Field of Classification Search .................. None
See application file for complete search history.

(56) References Cited

U.S. PATENT DOCUMENTS 5,919,665 A * 7/1999 Williams .................. 435/71.1

OTHER PUBLICATIONS

Zhou et al. (Prot. Exp. Pur., 34:8-16, 2004, available online on Dec. 19, 2003).*
Carstens et al. (Strategies Newsletter, 14:50-52, 2001).*
Baldwin et al. (Prot. Exp. Pur., 37:187-195, Sep. 2004).*
Lalli et al. (J. Cell Sci., 112:2715-2724, 1999).*
Baldwin, M., et al., "The C-terminus of botulinum neurotoxin type A light chain contributes to solubility, catalysis and stability", Protein Expr. Purif., 2004, 37:187-195.

* cited by examiner

*Primary Examiner*—Robert B Mondesi
*Assistant Examiner*—Brian J Gangle
(74) *Attorney, Agent, or Firm*—Quarles & Brady, LLP

(57) ABSTRACT

A method of producing botulinum toxin C-terminal receptor binding domain (HCR) is disclosed. The one embodiment, the method comprises the steps of (a) preparing *E. coli* transformed with an expression vector comprising DNA encoding HCR protein, (b) inducing expression of the HCR protein at a reduced temperature in a culture media, and (c) purifying the HCR protein via extraction, wherein the extraction comprises a clarification by centrifugation and a filtration, wherein the purified HCR protein is at least 10 mg/L of culture medium.

13 Claims, 4 Drawing Sheets

A

| HCR/A1 | HCR/A2 | HCR/E |

B

HCR/A1

| | | | SEQ ID NO |
|---|---|---|---|
| Peptide 1 | | | |
| BoNT/A1 | 1019 | ITNNRLNNSKIYI | 1031 1 |
| BoNT/A2 | 1019 | ITNNRLTKSKIYI | 1031 2 |
| BoNT/E | 995 | ITNDRLGDSKLYI | 1007 3 |
| | | *: .: | |
| Peptide 2 | | | |
| BoNT/A1 | 1074 | FDKELNEKEIKDL | 1086 4 |
| BoNT/A2 | 1074 | FDKELNEKEIKDL | 1086 4 |
| BoNT/E | 1049 | FDKELDETEIQTL | 1061 5 |
| | | *****:* **. * | |

FIG. 4

ESCHERICHIA COLI-DERIVED VACCINE AND THERAPY AGAINST BOTULISM

CROSS-REFERENCE TO RELATED APPLICATION

This application is a divisional of U.S. patent application Ser. No. 11/289,851 now abandoned filed Nov. 30, 2005, which claims benefit to U.S. Provisional Application 60/632,502 filed Dec. 2, 2004. These applications are incorporated by reference herein.

STATEMENT REGARDING FEDERALLY SPONSORED RESEARCH OR DEVELOPMENT

This invention was made with United States government support awarded by the following agencies: NIH AI57153. The United States has certain rights in this invention.

BACKGROUND OF THE INVENTION

The neurotoxins of *Clostridium botulinum* (BoNTs) are the most potent protein toxins for humans and are included in the list of Category A Select Agents and Toxins (14). BoNTs comprise seven distinguishable serotypes, A-G, with serotypes A, B, and E responsible for most natural human intoxications (19). Each BoNT serotype is classically defined by the specificity of antibody neutralization. Thus, antibodies that neutralize BoNT serotype A (BoNT/A) do not neutralize the toxicity of BoNT serotypes B-G.

Currently available vaccines are composed of chemically inactivated crude isolates of BoNTs. There are two available therapies against botulism, a pentavalent vaccine against serotypes A-E (20) and a heptavalent immune globulin against serotypes A-G (27). However, these vaccines are produced from chemically inactivated BoNT that is produced in *C. botulinum* and is currently in limited supply. There is a need to develop more efficient approaches for vaccine development against botulism.

BoNTs are zinc proteases that elicit flaccid paralysis by inhibiting the fusion of neurotransmitter-carrying vesicles to the plasma membrane of peripheral neurons. BoNTs are produced as ~150 kDa nontoxic single chain proteins that are activated by proteolytic cleavage to a dichain structure. BoNTs comprise three functional domains, organized as an N-terminal catalytic domain (Light Chain, LC), an internal translocation domain (Heavy Chain, HCT), and a C-terminal receptor binding domain (Heavy Chain, HCR) (FIG. 1A). In addition, HCR can be divided into a N-terminal domain ($HCR_N$) and a C-terminal domain ($HCR_C$).

$HCR_C$ has been implicated to possess receptor binding capacity for neurons (23). BoNTs enter neurons via receptor-mediated endocytosis. The neurotoxicity of BoNTs is due to the affinity of HCR for protein(s) on the plasma membrane of peripheral neurons (22). The HCR-plasma membrane receptor interaction is enhanced by gangliosides, which are low affinity co-receptors for HCR (12). The translocation capabilities of HCT have been extrapolated from the action of the translocation domain of diphtheria toxin (8). Both native and recombinant HC form channels in artificial lipid bilayers through which the LC can be translocated (17). Upon delivery into the cytosol, LC cleaves neurotransmitter vesicle docking proteins, BoNT/A cleaves SNAP25 between residues 197-198 and BoNT/E cleaves SNAP25 between residues 180-181, which inactivates SNAP25 (33).

In addition to the 7 serotypes of BoNT (A-G) (13, 16) several BoNT variants (sub-serotypes) have been identified that are immunologically distinguishable within a serotype. The classical type A-Hall strain (ATCC 3502) (BoNT/A1) and the Kyoto F infant strain (BoNT/A2) differ by ~10% in their primary amino acid sequence (10, 11, 15), while BoNT/$E_B$ and BoNT/$B_A$ possess ~92% primary amino acid homology.

New vaccine strategies for botulism based upon recombinant antigens are currently under development. Native and recombinant HCR purified from *C. botulinum* and *Escherichia coil* protect mice against BoNT/A challenge when administered intra-parenterally (i.p.) (29, 32). Currently the HCR domains of the BoNTs are being expressed in the yeast *Pichia pastoris* (26). While useful as a first generation recombinant BoNT vaccine, this approach has several limitations, including limited genetic manipulation (26).

BRIEF SUMMARY OF THE INVENTION

In one embodiment, the present invention is a method of producing botulinum toxin C-terminal receptor binding domain (HCR), comprising the steps of a) preparing *E. coli* transformed with an expression vector comprising DNA encoding at least 95% of the HCR protein, b) inducing expression of the HCR protein at a reduced temperature in a culture media, and c) purifying the HCR protein via extraction, wherein the extraction comprises a clarification by centrifugation and a filtration, wherein the purified HCR protein is at least 10 mg/L of culture medium, preferably at least 15 mg/L.

In one embodiment, the *E. coli* strain is *E. coli* BL-21 RIL, and the expression vector is a pET expression vector resulting in an N-terminal $HIS_6$-HCR/A fusion protein.

In one embodiment, the HCR protein is obtained from botulinum neurotoxin type A HCR protein.

In another embodiment, the HCR domain is obtained from botulinum neurotoxin types A, B, C, D, E, F and G.

Other embodiments, aspects and advantages of the present invention will be apparent to one of skill in the art after review of the specifications, claims and drawings.

BRIEF DESCRIPTION OF THE SEVERAL VIEWS OF THE DRAWINGS

FIG. 4. Protein modeling of HCR/A2 (Kyoto F) and HCR/E (Beluga). (A) Using the structures of BoNT/A (pdb: 3bta), BoNT/B (pdb:1epw), and Tetanus HCR (pdb:1doh) as templates, the 3-D structures of HCR/A2 and HCR/E$_B$ were generated using Swiss-Model. Ribbon diagrams of HCR/A1 (blue), HCR/A2 (red) and HCR/E$_B$ (black) are displayed in the upper panels. Molecular surface electrostatic potentials of each protein were computed using the Coulomb method and are displayed in the lower panels (blue, positive charge; red, negative charge; white, neutral). The regions of lowest structural homology between HCR/A1, HCRA2 and HCR/E are circled and labeled 1-4. (B) Enlarged view of region 5 highlighting the primary residues contributing to the electrostatic surface of the molecule (Left panel). Sequence alignment of the peptides forming this region are displayed on the right with conserved charge residues highlighted.

DESCRIPTION OF THE INVENTION

Figure 1:
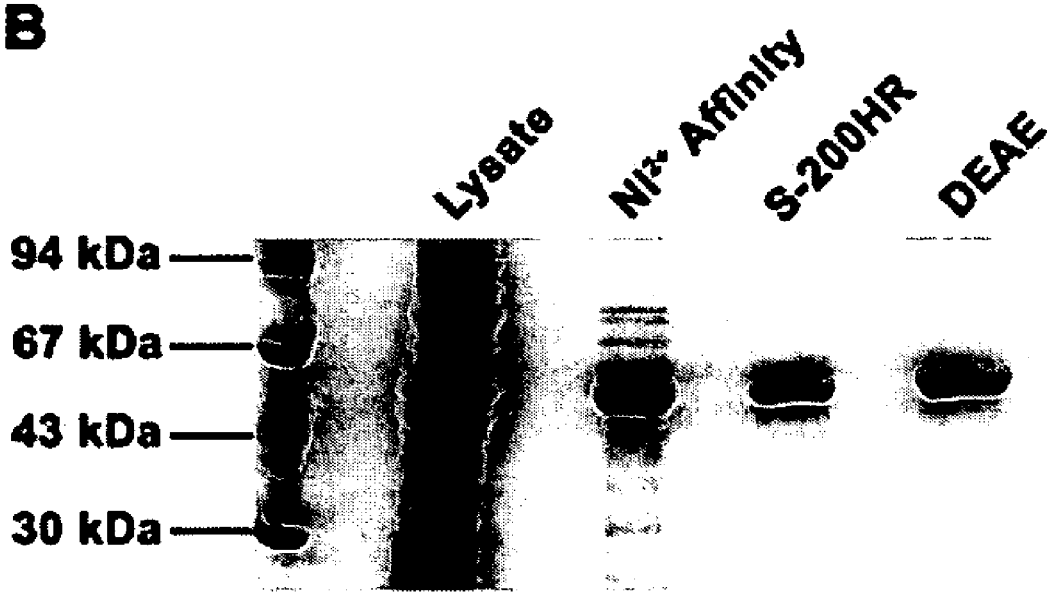
FIG. 1. Purification of recombinant HCR/A1. (A) BoNT/A1 is cleaved by Clostridial proteases into a dichain toxin that are linked by a disulfide bond. The N-terminal light chain (LC) encodes a zinc protease. The C-terminal heavy chain (HC) includes a translocation domain (HCT), and a C-terminal receptor binding domain (HCR) which can be sub-divided into an N-terminal ($HCR_N$) and C-terminal domain (denoted ΔA). (B) rHCR/A1 was purified from *E. coli* cell paste by a three column strategy. The clarified extract was purified sequentially using Nickel affinity, gel filtration and ion exchange chromatography. rHCR/A (5 μg) was separated by SDS-PAGE under reducing conditions and visualized by staining with silver.

We describe herein and in the Examples below an *Escherichia coli*-derived vaccine and therapy against botulism.

Botulinum toxins are zinc proteases that elicit paralysis by inhibiting the fusion of neurotransmitter-carrying vesicles to the plasma membrane of peripheral neurons. The toxins are produced as approximately 150 kDa non-toxic single chain proteins that are activated by proteolytic cleavage to a dichain structure. Botulinum neurotoxins are composed of three functional domains: an N-terminal catalytic domain (Light Chain, LC), an internal translocation domain (Heavy Chain, HCT), and a C-terminal receptor binding domain (Heavy Chain, HCR). One should examine Lacy, D. B., Stevens, R. C., Sequence homology and structural analysis of the costridial neurotoxins, J. Mol. Biol. 1999, Sep. 3:291(5): 1091-1104, incorporated by reference herein, for description of the boundaries of the different domains.

In one embodiment, the present invention is the expression and preparation of the botulinum neurotoxin HCR from *E. coli* at a concentration of at least 10 mg of total HCR per liter of culture, and preferably 15 mg/L after initial extraction. Preferably, the concentration will be between 10 mg-100 mg per liter. As described below, the method preferably comprises growing and inducing the bacteria at a particularly advantageous temperature and extracting the protein in the presence of a reducing agent.

The methods and compositions of the present invention are meant to encompass all seven serotypes and subtypes within the seven serotypes of botulinum neurotoxin. (See Lacy, et al., 1999, supra, for a description of serotypes and subtypes. The Examples below describe the subcloning of the receptor binding domain (HCR) of botulinum neurotoxin type A. One of skill in the art would readily find the corresponding nucleotides to create a clone in the other botulinum serotypes and subtypes. For example, such information is available in databases such as GenBank. In a general form of the present invention, one would first clone DNA encoding an HCR portion of a botulinum toxin into an expression vector. For example, the Examples below describe the sub-cloning of residues 870 through 1295 of BoNT/A/(HCR/A) from *C. botulinum* strain ATCC 3502 into a modified pET28a (Novagen) expression vector that contained unique KpnI and PstI sites.

One might wish to subclone less than the full HCR sequence. In another embodiment of the invention, one would subclone at least 95%, preferably 98%, of the native HCR sequence into the cloning vector.

The expression vector is then introduced into an *E. coli* strain, preferably *E. coli* BL-21 RIL. Preferable strains include those, such as BL-21 and its commercially available derivatives, that are suitable for over-expressing proteins. BL-21 series of *E. coli* hosts are protease deficient and designed for high-level protein expression from T7 RNA polymerase-based expression systems. These strains naturally lack the Lon protease, are engineered to be deficient for the OmpT protease and are derived from *E. coli* B. The Lon and OmpT proteases found in other *E. coli* expression hosts are thought to interfere with the isolation of intact recombinant proteins.

The *E. coli* strain carrying the expression vector is typically grown overnight and then inoculated into a growth medium, and the expression of the HCR gene is induced at a reduced temperature, preferably between 16-18° C. and preferably overnight.

Expression at reduced temperature and extraction with a reducing agent, such as DTT, and gel filtration with triton, preferably 0.5-2%, provided the maximum amount of soluble protein. The specific cloning vector used is not critical.

Cells are harvested and lysed in a buffer preferably comprising a reducing agent, preferably DTT at 0.5-10 mM. One could also use other reducing agents such as reduced glutathione or B-mercaptoethanol. We use 1 mM DTT to optimize the extraction of the HCR from the extract while allowing binding to NTA column.

The cell lysate is typically clarified by centrifugation and passed through a filter to remove unbroken bacteria. The examples below disclose a preferred filter, a 0.45 μm filter. However, filters of 0.2 μm-2 μm would be suitable.

The filtered lysate ("initial extraction") may be loaded onto a column, preferably an Ni-NTA resin column, and the HCR protein eluted. Fractions from the column may be combined, clarified by centrifugation and subjected to gel filtration.

We believe that the method of the present invention results in an unexpectedly robust concentration of protein. Total protein after initial extraction will be at least 10 mg/L and preferably 15 mg of total HCR per liter of culture medium and will be at least 13 mg/L of culture after gel filtration. Protein concentrations are typically determined using a bovine serum albumin (BSA) standard. There are other suitable methods.

The compositions of the present invention are expected to be useful as a vaccine and as a therapeutic agent.

EXAMPLES

Methods

Materials. All chemicals were from Sigma-Aldrich unless otherwise stated. Restriction enzymes and DNA polymerases were from Invitrogen. BoNT/A, and E were purified as described previously (9, 30).

Construction of rHCR/A and rHCR/E gene. Total genomic DNA from *C. botulinum* strain ATCC 3502 (Hall A) was used as a template to amplify full length HC/A (residues 449-1295). The PCR product was ligated into the TA cloning vector, pGEM-T (Promega), and the nucleotide sequence of the cloned insert verified. pGEM-HC/A was subsequently used as a template to generate expression constructs. The DNA fragment encoding HCR/A, containing residues 870-1295 of BoNT/A, was amplified and sub-cloned into a modified pET28a (Novagen) expression vector that contained unique KpnI and PstI sites. A similar cloning strategy was used to construct HCR/A2 (residues 871-1295) and HCR/E (residues 844-1250) using DNA from C. botulinum strains Kyoto F and Beluga, respectively.

rHCR expression in E. coli. Purification protocols for rHCR/A1, rHCR/A2, rHCR/$E_B$, rHCR$_C$/A1 (ΔA) and HCR$_C$/$E_B$ (ΔE) were identical and are described for rHCR/A1. pET28-HCR/A1 was transformed into E. coli BL-21 RIL (DE3) (Stratagene). E. coli BL-21 RIL (DE3) (pET28-HCR/A) was grown overnight on LB-agar with 50 μg/ml kanamycin and 50 μg/ml chloramphenicol. Cells were inoculated into LB-medium containing the same antibiotics, grown at 30° C. for 2.5 hours at 250 rpm to $OD_{600}$~0.6, induced by addition of 1 mM IPTG, and then cultured at 250 rpm overnight at 16° C. Cells (5×0.4 L cultures) were harvested and lysed with a French Press (2-3 times) in 40 ml ice cold buffer A (1 mM DTT, 10 mM imidazole, 500 mM NaCl, 20 mM Tris-HCl, pH 7.9) containing EDTA-free protease inhibitor cocktail, 1 mM PMSF and 2.5 μg/ml DNAse I and 2.5 μg/ml RNAse A. The lysate was clarified by centrifugation at 20,000×g for 30 min at 4° C. and subsequently passed through a 0.45 μm filter. The filtered lysate was loaded onto a column of $Ni^{2+}$-NTA resin (5 ml bed volume, Qiagen) that had been equilibrated with 25 ml buffer A containing protease inhibitors. The column was washed with 40 ml buffer A followed by 20 ml buffer B (20 mM imidazole, 500 mM NaCl, 20 mM Tris-HCl, pH 7.9) and then eluted with 10×1 ml buffer C (250 mM imidazole, 500 mM NaCl, 20 mM Tris-HCl, pH 7.9). Peak fractions from the Nickel column were pooled, clarified by centrifugation at 12,000×g for 20 min at 4° C. and subjected to gel-filtration using Sephacryl S200 HR (300 ml column equilibrated in buffer D (1 mM EDTA, 20 mM NaCl, 20 mM Tris-HCl, pH 7.9, 0.1% Triton X-100). Peak fractions were subjected to anion exchange chromatography (DEAE-sephacel, 5 ml). rHCR passed through the column in the void volume, which was pooled, concentrated, and dialyzed overnight into PBS/40% v/v glycerol (FIG. 1B and Table 1).

MALDI-TOF mass spectroscopy of rHCR/$E_B$. Fifteen micrograms rHCR/$E_B$ (3 independent preparations) was excised from a SDS-PAGE gel and subjected to trypsin digestion (1 μg, Promega) in 50 μl of 100 mM $NH_4HCO_3$, pH 8, at 37° C. for 24 h. After digestion, gel slices were sonicated twice in 200 μl of 80% acetonitrile and 1% formic acid (in $H_2O$) for 10 min. Eluted material was combined and evaporated, and the pellet was dissolved in 15 μl of 0.1% trifluoroacetic acid (in $H_2O$). Peptide solutions were desalted with C18 Zip Tips (Millipore) that had been equilibrated successively in 15 μl of 100% acetonitrile, 15 μl of 50% acetonitrile ($H_2O$), and 15 μl of 0.1% trifluoroacetic acid in $H_2O$. Resin was washed twice with 0.1% trifluoroacetic acid in $H_2O$. Peptides were eluted in 2 μl of 60% acetonitrile and 0.1% trifluoroacetic acid ($H_2O$ saturated with -cyano-4-hydroxy-cinnamic acid) and applied to a sample plate to air dry. Samples were ionized by an $N_2$ UV laser using a PE-pro mass spectrometer (Applied Biosystems). Two hundred laser shots were conducted at an accelerating voltage of 25,000 V and laser intensity of 2075 (repetition rate 3 Hz). Scans were processed using Biosystems Voyager 6004 software. Peptide fingerprinting was used to identify the proteins present in the sample, using Protein Prospector (University of California at San Francisco).

Immunization of rabbits and mice with recombinant HCR fragments. Rabbit antisera against rHCR/A1 and rHCR/E were prepared by Covance, Inc. Briefly, female ELITE NZW rabbits were immunized intradermally with 250 μg rHCRs in Freund's complete adjuvant (day 0), boosted at days 14, 35, 49 and 70 with 125 μg rHCRs in Freund's incomplete adjuvant and terminally bleed at day 80.

Female ICR mice (18-22 g) were immunized intraperitoneally with 16.7 μg and subcutaneously with 3.3 μg of rHCR/A1 or rHCR/$E_B$ mixed with an equal volume of Alhydrogel as adjuvant. Mice were vaccinated at 0, 7, and 14 days. Four days after the final boost mice were challenged with the indicated amount of BoNT/A1, BoNT/A2 or BoNT/$E_A$ and monitored for 96 hours at which point survival was scored.

Serum Neutralization Assay. Potencies of BoNT; A1 Hall BoNT, 30-40 pg/$LD_{50}$ or $3.3 \times 10^7$-$2.5 \times 10^7$ $LD_{50}$ per mg tosin; A2 Kyoto F toxin, 15-20 pg/$LD_{50}$ or $6.67 \times 10^7$ to $5 \times 10^7$ $LD_{50}$ per mg toxin; E Alaska dichain toxin: 15-20 pg/$LD_{50}$ or $6.67 \times 10^7$ to $5 \times 10^7$ $LD_{50}$ per mg toxin. Four ng of BoNT/A1 (129 mouse $LD_{50}$) or 8 ng BoNT/$E_A$ (457 mouse $LD_{50}$) were incubated with serial dilutions of rabbit anti-rHCR/A1 or anti-rHCR/$E_B$ serum/ng toxin: (0.94 μl/ng, 0.75 μl/ng, 0.625 μl/ng, 0.5 μl/ng, 0.375 μl/ng, 0.3125 μl/ng, 0.25 μl/ng, 0.188 μl/ng, 0.125 μl/ng, and 0.0625 μl/ng). After a 2 hr incubation at RT, samples were injected into 3 female ICR mice (18-22 g), using a volume of 100 μl/mouse. Mice were monitored for 96 hours and survival was scored. These experiments were approved by an animal care-and-use committee at the University of Wisconsin at Madison.

ELISA. rHCRs were diluted to 1 μg/ml in coating buffer (50 mM $Na_2CO_3$, pH 9.6) and 100 μl was added to each well of an enhanced binding ELISA plate (Corning, EIA/RIA High binding plate) and allowed to adhere overnight at 4° C. Column 1 was incubated with coating buffer alone (No antigen control). Plates were then washed 4 times with 400 μl PBS and blocked for 1 hr at 37° C. with 200 μl per well 2% (w/v) BSA in coating buffer. Following a washing step as outlined above, plates were incubated for 1 hr at 37° C. with serial dilutions of the sera in binding buffer (1% BSA (w/v) in PBS, 100 μl per well). As controls, column 1 (no antigen) was incubated with the lowest dilution of the serum, while column two (No primary antibody) was incubated with binding buffer alone. Following a washing step, plates were incubated for 1 hr at 37° C. with either Donkey Anti-Mouse or Donkey Anti-Rabbit IgG-HRP conjugate (1:12000) in binding buffer. Plates were washed ×6 with 400 μl PBS and then incubated with 100 μl per well tetramethyl benzidine (TMB, Pierce) as substrate. The reaction was terminated by addition of 100 μl per well 0.1 M sulfuric acid and absorbance read at 450 nm using an ELISA plate reader (Wallac).

Results

HCR expression in E. coli. Although the production of recombinant fusion proteins in E. coli is well established, there are several factors which are obstacles for successful production and purification of soluble fusion proteins. While prior expression of botulinum neurotoxin components in E. coli has been reported, low yields and/or poor solubility has limited their use for biochemical analysis and vaccine development (7). We recently developed an expression strategy for the production of large amounts of recombinant BoNT/A LC (2), which prompted a re-evaluation of the potential to produce high yields of purified HCR in E. coli.

DNA encoding BoNT/A1 residues 870-1295 was subcloned into a pET expression vector resulting in an N-terminal $His_6$-HCR/A fusion protein (rHCR/A1). While rHCR/A expression was detected in E. coli BL21(DE3), enhanced expression was achieved in E. coli BL-21 (DE3)-RIL, which has been engineered for expression of AT-rich genes. As was reported for the LC of BoNT/A1 (2), induction at 16° C. was critical for the stable accumulation of rHCR/A to a concentration of ~20 mg/l culture. Expression of recombinant forms of BoNT/A2 and BoNT/E HCR has not been reported. Utilizing the expression conditions established for rHCR/A1; rHCR/A2 and rHCR/E$_B$ (Beluga strain, residues 844-1250) were expressed at levels comparable to rHCR/A1.

Purification of rHCR from *E. coli*. rHCR/A1, rHCR/A2 and rHCR/E$_B$ were purified by sequential chromatography on Ni$^{2+}$-NTA resin, gel filtration, and anion exchange. By gel-filtration analysis, the majority of the rHCR/A1 and A2 migrated as a monomer, while rHCR/E migrated as a dimer. Due to basic isoelectric points neither rHCR/A1, rHCR/A2, nor rHCR/E bound to DEAE resin at pH 7.9. Passing rHCR/A1, rHCR/A2 or rHCR/E through DEAE resin removed several contaminants, most notably a protease activity. A typical purification from a 1-liter culture yielded ~15-20 mg rHCR/A1, rHCR/A2 or rHCR/E$_B$ which were >95% pure as determined by SDS-PAGE (FIG. 1/Table 1). rHCR/A1, rHCR/A2, and rHCR/E$_B$ did not degrade upon storage in 10 mM Tris (pH 7.6)/20 mM NaCl at 4° C. after > one week or at −20° C. for several months.

Neutralizing capacity of rabbit α-rHCR antibodies. The neutralizing capacity of polyclonal rHCR/A1 and rHCR/E$_B$ serum to the homologous BoNT was determined using a mouse bioassay, where a LD$_{50}$ corresponds to the quantity of BoNT introduced via intra-peritoneal (i.p.) injection that resulted in 50% death after 4 days (29). BoNT/A1 used in this analysis had ~3.3×10$^4$ LD$_{50}$/μg while BoNT/E used in this analysis had ~1.2×10$^4$ LD$_{50}$/μg. Two independent α-rHCR/A1 sera neutralized ~5-7×10$^5$ mouse LD$_{50}$ of BoNT/A1/ml serum, while α-rHCR/E$_B$ neutralized between 1-3×10$^5$ mouse LD$_{50}$ of BoNT/E$_A$/ml serum. The Alaska subtype E of BoNT/E was used in challenge experiments, since purification of this subtype from *C. botulinum* is more efficient than the Beluga subtype of BoNT/E. Controls showed that neither anti-rHCR/A1 nor α-rHCR/E$_B$ sera neutralized BoNT/B and that sera from pre-bleeds did not neutralize BoNT/A1 or BoNT/E$_A$. Using the mouse bioassay, α-rHCR/A1 sera did not neutralize BoNT/E$_A$, but α-rHCR/E$_B$ sera neutralization of BoNT/A1 could be observed (~1×10$^3$ mouse LD$_{50}$/ml). Although not directly comparable due to different immunization protocols, the neutralizing capacity of the sera was similar to that of humans vaccinated with the pentavalent BoNT toxoid (31).

Figure 2:
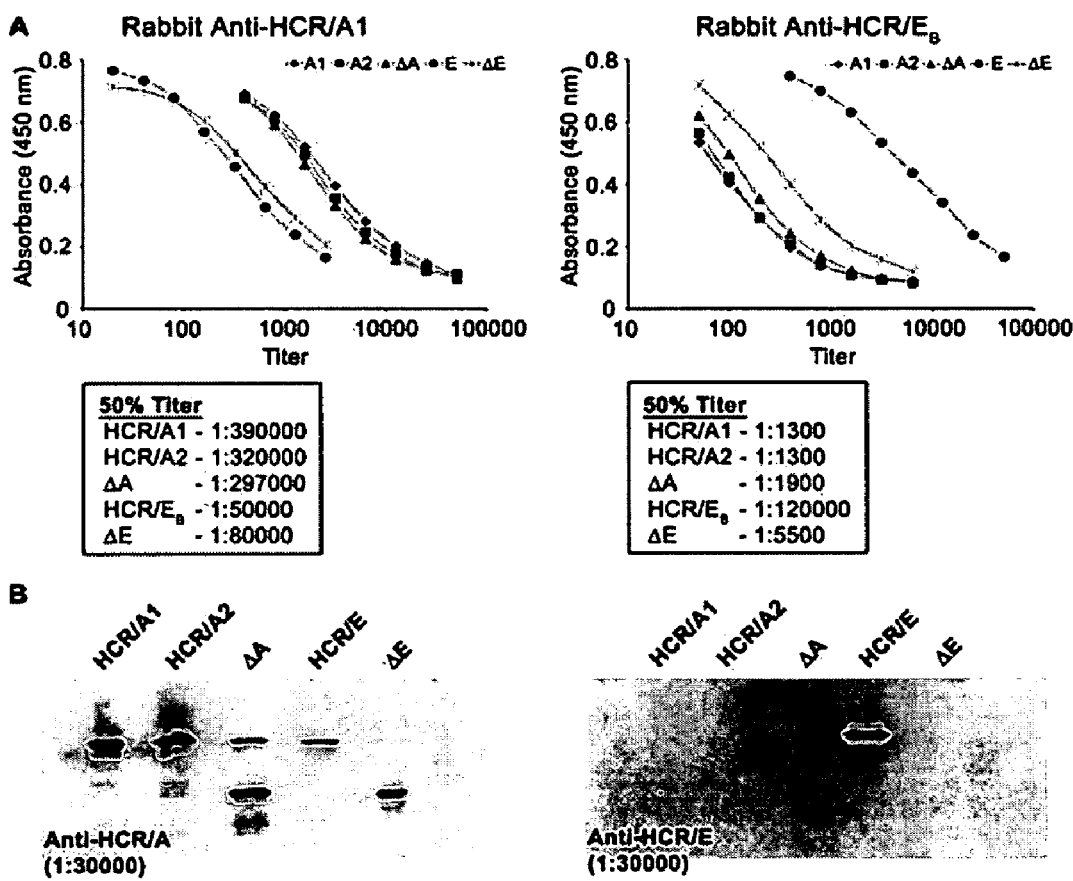
FIG. 2. Immunological characterization of rabbit sera against rHCR/A1 and rHCR/$E_B$. (A) ELISA of rabbit antisera to rHCR/A1 (Left panel) or rHCR/$E_B$ (right panel), using 100 ng rHCR/A1, 100 ng rHCR/A2, 100 ng rHCR/ΔA, 100 ng rHCR/$E_B$ and 100 ng rHCR/ΔE as capture antigens. (B) Antigens (500 ng) were separated by SDS-PAGE under reducing conditions and visualized by Western blotting with anti-rHCR/A1 sera (Left panel) or anti-rHCR/$E_B$ (Right panel).

Immunoreactivity of rabbit anti-rHCR antibodies. Reactivity of the α-rHCR sera was tested against rHCR/A1, rHCR/A2 and rHCR/E. C-terminal peptides of the HCRs (BoNT/A1 residues 1090-1295, termed ΔA) and BoNT/E (residues 1065-1250, termed ΔE) were also tested for reactivity to localize antigenic epitopes. Western blot analysis showed that rabbit α-rHCR/A1 sera reacted against rHCR/A1, rHCR/A2 and ΔA with similar reactivity and also cross-reacted with rHCR/E$_B$ and ΔE (FIG. 2). ELISA showed that rabbit α-rHCR/A1 sera reacted with rHCE/E and ΔE at ~a 5-fold lower titer than the rHCR/A antigens. These data indicated that epitope(s) within the C terminus of HCR were immune dominant when rHCR/A1 was used as an immunogen.

Two independent rabbit α-rHCR/E$_B$ sera displayed distinctive immune reactive properties relative to the reactivity of the α-rHCR/A1 sera. Western blot analysis showed that rabbit α-rHCR/E$_B$ sera reacted against rHCR/E$_B$, but did not react with ΔE or the serotype A antigens. ELISA showed that the rabbit α-rHCR/E$_B$ sera titers to ΔE and the type A antigens was detected, but with between 10 and 50-fold lower titers than for rHCR/E. These data indicated that epitopes(s) within the N terminus of rHCR/E$_B$ or at the interface of the N-terminal and C-terminal domains were the major epitopes of rHCR/E$_B$. Thus, although HCR/A and HCR/E are 44% identical, the two antigens generated a unique immune response and cross protective antibodies in rabbits.

Immune protection of rHCR against BoNTs. The neutralizing capacity and unique serum cross-reactivity of the rabbit α-rHCR sera promoted subsequent studies to determine the efficacy of rHCR/A1 and rHCR/E$_B$ as vaccine candidates against homologous and heterologous BoNT serotype challenge.

Low dose immunization. Mice were immunized with rHCR/A1 or rHCR/E$_B$ in aluminum hydroxide adjuvant (Al-hydrogel) and challenged with homologous and heterologous serotypes of BoNT. Immunization with rHCR/A1 or rHCR/E did not elicit distress in mice. Mice immunized with rHCR/A1 were resistant to challenge with up to 100,000 LD$_{50}$ of either BoNT/A1 or BoNT/A2, but not BoNT/E (Table 2). This is the first demonstration that immunization with the classical type A HCR protects against challenge by a heterologous sub-serotype of BoNT/A. Similarly, mice immunized with rHCR/E$_B$ were resistant to challenge with up to 100,000 LD$_{50}$ of BoNT/E$_A$ but not either BoNT/A1 or BoNT/A2.

Hyper immunization. In other experiments, mice were immunized with 20 μg of rHCR/A1 or rHCR/E$_B$ to determine the effect of hyper immunization on the protective response. Mice immunized with rHCR/A1 were resistant to challenge with 100,000 mouse LD$_{50}$ BoNT/A1, BoNT/A2, but remained sensitive to BoNT/E$_A$. Mice immunized with rHCR/E were resistant to challenge with 100,000 mouse LD$_{50}$ BoNT/E and were protected against challenge with 10 mouse LD$_{50}$ of BoNT/A1 or BoNT/A2. In one experiment 6 of 6 mice challenged were protected, while in another experiment 3 of 3 mice displayed a delay in time to death.

Figure 3:
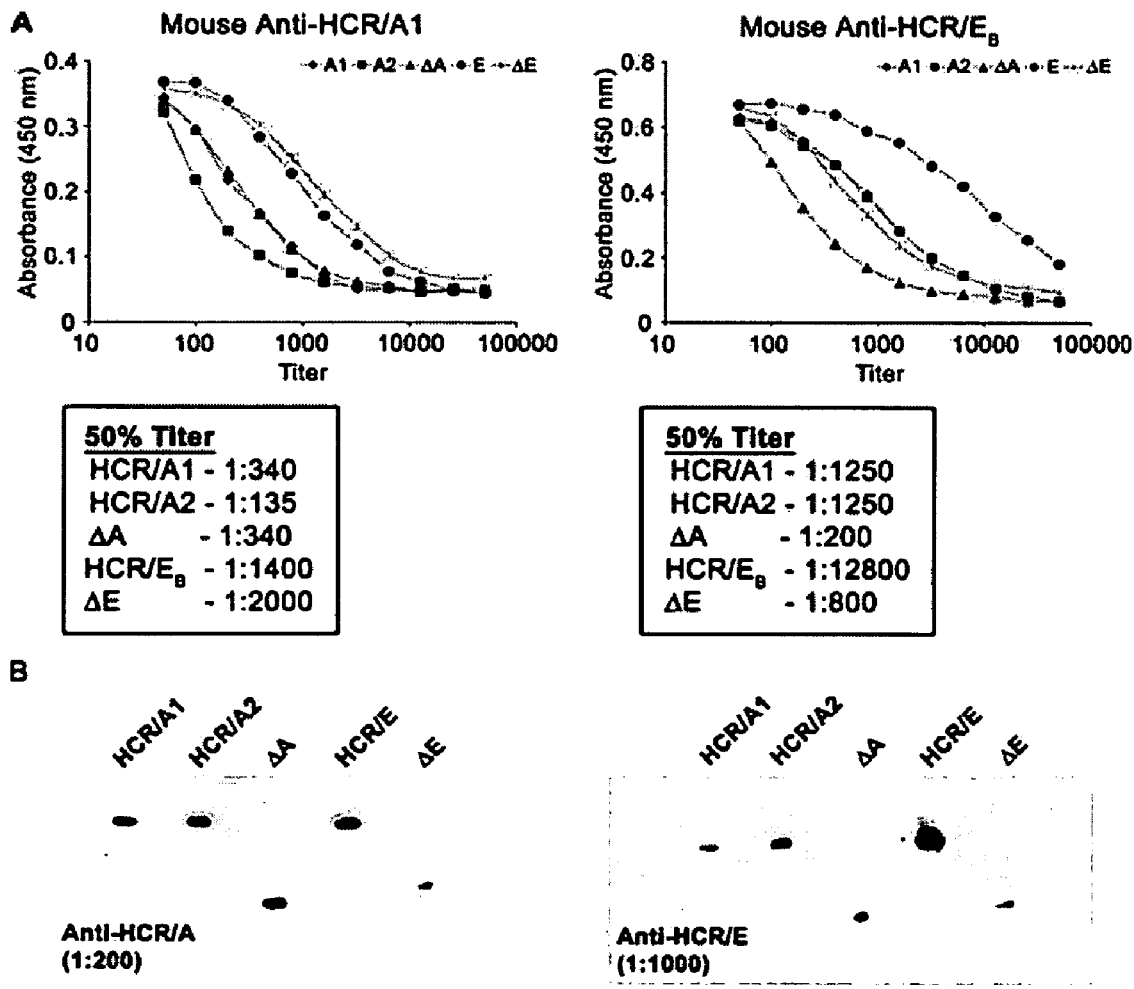
FIG. 3. Immunological characterization of mouse sera against rHCR/A1 and rHCR/$E_B$. (A) ELISA of mouse antisera to rHCR/A1 (Left panel) or rHCR/E$_B$ (right panel), using 100 ng rHCR/A1, 100 ng rHCR/A2, 100 ng rHCR/ΔA, 100 ng rHCR/E$_B$ and 100 ng rHCR/ΔE as capture antigens. (B) Antigens (500 ng) were separated by SDS-PAGE under reducing conditions and visualized by Western blotting with anti-rHCR/A1 sera (Left panel) or anti-rHCR/E$_B$ (Right panel).

Immunoreactivity of mouse anti-rHCR antibodies. Pooled sera isolated from mice immunized with either a low or high amount of HCR was analyzed by Western blotting and ELISA. α-rHCR/A1 sera from mice immunized with 20 μg of antigen reacted against rHCR/A1, rHCR/A2, ΔA by Western blot and displayed reactivity to rHCR/E and to a lesser extent ΔE (FIG. 3). ELISA revealed differences in the relative reactivity of mouse α-rHCR/A1 sera to these antigens where reactivity to HCR/E$_B$ and ΔE was ~10-fold higher than recognition of the type A antigens. Mouse α-rHCR/A1 sera from mice immunized with low does of antigen (2.5 μg of antigen) displayed similar Western blot and ELISA profiles, although overall titers were 2-3 fold lower than observed for the sera from mice immunized with 20 μg of antigen (data not shown).

Western blot analysis of α-rHCR/E sera from hyperimmunized mice with 20 μg of rHCR/E$_B$ showed reactivity to rHCR/E$_B$ and to a lesser extent with ΔE and the A serotype antigens. ELISA of mouse α-rHCR/E sera showed that the reactivity to rHCR/E was ~8-fold higher than ΔE, rHCR/A1 and rHCR/A2, and ~16-fold higher than ΔA. Sera from animals immunized with lower doses of rHCR/E (2.5 μg of antigen) displayed similar Western blot and ELISA profiles, although reactivity to all antigens was 2-fold lower than observed for the sera from mice immunized with 20 μg of antigen (data not shown).

Purity of rHCR/E. The cross serotype protection of serum immunized with rHCR/E$_B$ against BoNT/A1 and BoNT/A2 raised the possibility that rHCR/E$_B$ was contaminated with rHCR/A1. To address this concern, the purity of the rHCR/E$_B$ preparation used for rabbit antibody production and mouse vaccine development was determined. Fifteen μg of rHCR/E$_B$ was subjected to SDS-PAGE followed by in-gel tryptic digestion. MALDI/MS analysis identified ~75% of the predicted tryptic peptides of rHCR/E$_B$, but did not identify any tryptic peptides that were unique to rHCR/A1. Moreover, further analysis of two independently prepared preparations of rHCR/E$_B$ by both MALDI/MS and ELISA produced identical tryptic peptides and immune reactivity, respectively. This indicates that the cross protection elicited by rHCR/E$_B$ is intrinsic to the protein and not due to cross contamination among protein preparations.

Structural basis for the cross protection elicited by HCR/A and HCR/E. Despite the relatively low primary amino acid homology among the BoNTs (30-50% identity), the crystal structures of HCRs of BoNT/A1, BoNT/B and tetanus toxin share overall structural similarity (16). Using Swiss Modeler, the predicted structures of HCR/A2 (Kyoto F, 90% identity to HCR/A1) and HCR/E$_B$ (Beluga, 44% identity to HCR/A1) were determined. While HCR/A1, HCR/A2 and HCR/E$_B$ showed similar overall topology to their templates BoNT/A1, BoNT/B and tetanus HCR (FIG. 4A, upper panel), four regions (1-4) between HCR/A1 and HCR/E showed low structural homology. These loops were located at interface of the sub-domains of HCR (loops 1, 2, and 4) or towards the C terminus of the molecule. Since these loop regions represent the only major structural differences between HCR/A and HCR/E, these loops may represent epitope(s) for serological distinction.

The surface electrostatic potential of HCR/A1, HCR/A2 and HCR/E was also calculated (FIG. 4A, lower panel). The charge distribution of HCR/A1 and HCR/A2 were similar, with an acidic C-terminal domain surface and a basic/neutral N-terminal domain surface. HCR/E$_B$ showed a different distribution of surface electrostatic potential relative to HCR/A. The C-terminal domain surface was highly basic, while the surface of the N-terminal domain was primarily neutral. However, one region of charge conservation was identified in the N-terminal domain (position 5). The acidic surface potential within this region results from both structural and primary amino acid conservation region (see FIG. 4B). Thus, this region could represent a common conformational epitope among the A and E serotypes of BoNT.

Discussion

The botulinum neurotoxins can be beneficially employed for the treatment of several involuntary muscle disorders, but have also been given high priority for the development of vaccines and therapies to prevent intoxication (1). Botulism can be prevented by administration of neutralizing antibodies or vaccination. The licensed trivalent antitoxin contains neutralizing antibodies against botulinum toxin types A, B, and E, the serotypes that most commonly cause of human botulism. Passive immunity is currently provided through administration of equine antitoxin distributed by the CDC. While only limited data is available on the safety of current BoNT vaccines, studies of recipients of equine botulinum antitoxin in the United States demonstrate various acute reactions (4). The current vaccine is a pentavalent botulinum toxoid (A-E), which is effective but has several limitations including cost, efficacy and accessibility. Exposure to other serotypes of BoNT can be addressed with an investigational heptavalent (ABCDEFG) antitoxin (15).

Previous studies have indicated that major protective epitopes of BoNT/A are located in the receptor-binding domain (HCR) (7, 25). Thus, the use of HCR/A has been included in strategies for botulinum antibody therapy and vaccine development. The HCR component of BoNTs has several potential advantages over currently available C. botulinum-derived antigens. Production of HCR in a heterologous system facilitates large scale production and removes the possibility of contamination with other neurotoxins and clostridial components. This strategy was originally applied to BoNT/A, using an E. coli-based expression system (7). HCR/A expressed and purified from E. coli protected mice against challenged with active toxin. Moreover, purified HCR/A was as efficacious in protecting against challenge with BoNT/A as the pentavalent toxoid vaccine. Thus, HCR/A had the properties required for use as a vaccine candidate. However, in these early studies HCR/A was not expressed at levels sufficient for vaccine development and so was not pursued further. The limited utility of HCR/A expressed in E. coli prompted the development of the methylotrophic yeast Pichia pastoris as a heterologous host for expression of HCR fragments (5, 6). rHCR/A expressed in P. pastoris is highly immunogenic and induces protective immunity in mice and represent a useful first generation for vaccine development, but expression of HCRs in P. pastoris can be a challenge with respect to genetic manipulation and ease of purification (26). Popoff and coworkers have recently expressed HCR/A in E. coli and mapped the major protective epitopes of the BoNT to HCR (32).

The C. botulinum A Hall-hyper (28) has been used widely for the production of BoNT/A vaccines, studies on neurotoxin biochemistry, pharmacology and crystallography (18, 24) and in the manufacture of therapeutic BoNT. Comparison of the BoNT/A amino acid sequences from C. botulinum type A-Hall-hyper strain with other BoNT/A sequences revealed sub-types within serotype A (1, 10, 11). BoNT produced by the Kyoto F strain shares ~90% identity with the Hall-A strain and has been designated as BoNT/A2. These findings have raised the question of whether an antigen based upon a single strain can protect against all strain variants. The current study addresses this concern by showing that vaccination with rHCR/A1 protected against challenge by both BoNT/A1 and BoNT/A2. While several serotypes of BoNT HCR have been used in vaccine development, HCR/E derived vaccines are currently lacking. Here we report for the first time that rHCR/E$_B$ elicits protective immunity to BoNT/E$_A$. In these experiments HCR/E engineered from the Beluga sub-type protected from challenge with the BoNT/E from the Alaska strain of C. botulinum. This shows efficient protection from immunization with heterologous HCR/E sub-types.

Classically, botulinum serotypes are defined by the lack of cross-protection between neutralizing anti-sera, i.e. anti-type A sera does not neutralize BoNT from other serotypes. The cross protection elicited by hyper immunization with HCR/E to BoNT/A1 intoxication suggests the presence of cross protective epitope(s) within the BoNTs. The enhanced cross protection elicited by HCR/E$_B$ relative to HCR/A may be due to a polyclonal epitope response to the HCRs, where antibodies to multiple epitopes are required for neutralization (3) or may represent the expansion of a minor common epitope that is stimulated upon immunization with large amounts of antigen. While it is not practical to envision that this level of cross protection will yield a common protective immunogen using HCR subunit vaccination, identification of the mechanism responsible for this cross-protection may lead to the development of reagents with cross-neutralizing capabilities. Earlier studies by Middlebrook and coworkers reported some cross-protection of mice against BoNT/E when immunized by BoNT/A (7, 20).

Molecular modeling predicts the structures of HCR/A2 and HCR/E$_B$ (FIG. 4). HCR/A2 has ~90% homology with HCR/A1 and is predicted to have similar structures and overall electrostatic potential. This is consistent with the cross-protection observed with immunization with rHCR/A1. HCR/E$_B$ has 44% homology with HCR/A1. While the overall predicted structures are similar, HCR/A1 differs from HCR/E$_B$ in four loop regions (Loops 1-4), which are candidate epitopes for the differential protection elicited by HCR/E$_B$ relative to HCR/A1. HCR comprises two domains, the N-terminal domain (residues 870-1095) and the C-terminal domain (residues 1096-1295). The C-terminal domain has been proposed to include the receptor binding domain (21). Popoff and coworkers implicated a role for epitopes within the interface of these two domains of HCR for effective immunization (32). Thus loops 1, 2, and 4, which lie within the interface (FIG. 4), may define serotype specific neutralization epitopes. Alternatively, while predicted electrostatic properties of HCR/A1 and HCR/A2 are similar, HCR/A electrostatic properties are different from HCR/E and common regions of electrostatic potential may contribute to the common epitopes among the HCRs of the BoNTs. Current studies address the nature potential common neutralizing epitopes of BoNT/A and BoNT/E.

The immunogenic potency of *E. coli*-derived rHCRs represent tools that allow genetic manipulation to develop the next generation of vaccines and therapies against botulism, as well as reagents to elucidate the cell biology of BoNT intoxication of neurons. The sub-type protection elicited by HCR/A1 and HCRE$_B$ predicts that a well designed heavy chain subunit vaccine can protect against variant sub-types of the BoNTs.

LITERATURE CITED 1. 2002. NIAID: SUMMARY OF THE NIAID EXPERT PANEL ON BOTULINUM TOXINS. NIAID Publications.
2. Baldwin, M. R., M. Bradshaw, E. A. Johnson, and J. T. Barbieri. 2004. The C-terminus of botulinum neurotoxin type A light chain contributes to solubility, catalysis, and stability. Protein Expr Purif 37:187-95.
3. Berzofsky, J. A., Berkower, I. J., and Epstein, S. L., 1999. Antigen-Antibody Interactions and Monoclonal Antibodies, Fundamental Immunology Paul, W. E., ed: pp. 91-94.
4. Black, R. E., and R. A. Gunn. 1980. Hypersensitivity reactions associated with botulinal antitoxin. Am J Med 69:567-70.
5. Byrne, M. P., and L. A. Smith. 2000. Development of vaccines for prevention of botulism. Biochimie 82:955-66.
6. Byrne, M. P., T. J. Smith, V. A. Montgomery, and L. A. Smith. 1998. Purification, potency, and efficacy of the botulinum neurotoxin type A binding domain from *Pichia pastoris* as a recombinant vaccine candidate. Infect Immun 66:4817-22.
7. Clayton, M. A., J. M. Clayton, D. R. Brown, and J. L. Middlebrook. 1995. Protective vaccination with a recombinant fragment of *Clostridium botulinum* neurotoxin serotype A expressed from a synthetic gene in *Escherichia coli*. Infect Immun 63:2738-42.
8. Collier, R. J. 2001. Understanding the mode of action of diphtheria toxin: a perspective on progress during the 20th century. Toxicon 39:1793-803.
9. Dasgupta, B. R., L. J. Berry, and D. A. Boroff. 1970. Purification of *Clostridium botulinum* type A toxin. Biochim Biophys Acta 214:343-9.
10. Dineen, S. S., M. Bradshaw, and E. A. Johnson. 2003. Neurotoxin gene clusters in *Clostridium botulinum* type A strains: sequence comparison and evolutionary implications. Curr Microbiol 46:345-52.
11. Dineen, S. S., M. Bradshaw, C. E. Karasek, and E. A. Johnson. 2004. Nucleotide sequence and transcriptional analysis of the type A2 neurotoxin gene cluster in *Clostridium botulinum*. FEMS Microbiol Lett 235:9-16.
12. Dong, M., D. A. Richards, M. C. Goodnough, W. H. Tepp, E. A. Johnson, and E. R. Chapman. 2003. Synaptotagmins I and II mediate entry of botulinum neurotoxin B into cells. J Cell Biol 162:1293-303.
13. Gimenez, D. F. a. G., J. A. 1993. Serological subtypes of botulinal neurotoxins, in Botulism and tetanus Neurotoxins. Neurotransmission and Biomedical Aspects Ed. DasGupta, B. R., in Plenum Press, New York.
14. HHS. 2002. Possession, Use, and Transfer of Select Agents and Toxins. 42 CFR Part 73; 42 CFR Part 1003.
15. Hibbs, R. G., J. T. Weber, A. Corwin, B. M. Allos, M. S. Abd el Rehim, S. E. Sharkawy, J. E. Sarn, and K. T. McKee, Jr. 1996. Experience with the use of an investigational F(ab')2 heptavalent botulism immune globulin of equine origin during an outbreak of type E botulism in Egypt. Clin Infect Dis 23:337-40.
16. Izumi, N., H. Kondo, I. Ohishi, and G. Sakaguchi. 1983. Purification and characterization of alpha-toxin of *Clostridium oedematiens* type A. Jpn J Med Sci Biol 36:135-46.
17. Koriazova, L. K., and M. Montal. 2003. Translocation of botulinum neurotoxin light chain protease through the heavy chain channel. Nat Struct Biol 10:13-8.
18. Lacy, D. B., W. Tepp, A. C. Cohen, B. R. DasGupta, and R. C. Stevens. 1998. Crystal structure of botulinum neurotoxin type A and implications for toxicity. Nat Struct Biol 5:898-902.
19. Marvaud, J. C., S. Raffestin, and M. R. Popoff. 2002. [Botulism: the agent, mode of action of the botulinum neurotoxins, forms of acquisition, treatment and prevention]. C R Biol 325:863-78; discussion 879-83.
20. Middlebrook, J. L. 1995. Protection strategies against botulinum toxin. Adv Exp Med Biol 383:93-8.
21. Montecucco, C., O. Rossetto, and G. Schiavo. 2004. Presynaptic receptor arrays for clostridial neurotoxins. Trends Microbiol 12:442-6.
22. Montecucco, C., and G. Schiavo. 1994. Mechanism of action of tetanus and botulinum neurotoxins. Mol Microbiol 13:1-8.
23. Montecucco, C., and G. Schiavo. 1995. Structure and function of tetanus and botulinum neurotoxins. Q Rev Biophys 28:423-72.
24. Montecucco, C., G. Schiavo, V. Tugnoli, and D. de Grandis. 1996. Botulinum neurotoxins: mechanism of action and therapeutic applications. Mol Med Today 2:418-24.
25. Nowakowski, A., C. Wang, D. B. Powers, P. Amersdorfer, T. J. Smith, V. A. Montgomery, R. Sheridan, R. Blake, L. A. Smith, and J. D. Marks. 2002. Potent neutralization of botulinum neurotoxin by recombinant oligoclonal antibody. Proc Natl Acad Sci U S A 99:11346-50.
26. Potter, K. J., W. Zhang, L. A. Smith, and M. M. Meagher. 2000. Production and purification of the heavy chain fragment C of botulinum neurotoxin, serotype A, expressed in the methylotrophic yeast *Pichia pastoris*. Protein Expr Purif 19:393-402.
27. Robinson, R. F., and M. C. Nahata. 2003. Management of botulism. Ann Pharmacother 37:127-31.
28. Schantz, E. J., and E. A. Johnson. 1997. Botulinum toxin: the story of its development for the treatment of human disease. Perspect Biol Med 40:317-27.
29. Schantz, E. J., and E. A. Johnson. 1990. Dose standardisation of botulinum toxin. Lancet 335:421.
30. Schmidt, J. J., and L. S. Siegel. 1986. Purification of type E botulinum neurotoxin by high-performance ion exchange chromatography. Anal Biochem 156:213-9.
31. Siegel, L. S. 1988. Human immune response to botulinum pentavalent (ABCDE) toxoid determined by a neutralization test and by an enzyme-linked immunosorbent assay. J Clin Microbiol 26:2351-6.
32. Tavallaie, M., A. Chenal, D. Gillet, Y. Pereira, M. Manich, M. Gibert, S. Raffestin, M. R. Popoff, and J. C. Marvaud. 2004. Interaction between the two subdomains of the C-terminal part of the botulinum neurotoxin A is essential for the generation of protective antibodies. FEBS Lett 572:299-306.

33. Tonello, F., S. Morante, O. Rossetto, G. Schiavo, and C. Montecucco. 1996. Tetanus and botulism neurotoxins: a novel group of zinc-endopeptidases. Adv Exp Med Biol 389:251-60.

TABLE 1

Purification profile for *E. coli* expressed rHCR/A.

| rHCR/A | Total rHCR/A (mg/l culture)[a] | Total protein (mg/l culture)[b] | Purification Factor[b] | Yield (%) |
|---|---|---|---|---|
| Extraction | 17 | 525 | 1 | 100 |
| Ni-NTA | 15 | 18 | 14 | 88 |
| Gel filtration | 13 | 15 | 15 | 76 |
| Ion exchange | 12 | 12 | 44 | 71 |

Data are representative of 2 independent determinations
[a]Estimated from band intensity on SDS-PAGE
[b]Based on total protein content

TABLE 2

Protection from BoNT intoxication by rHCR[a]

| Immunization (2.5 µg antigen) | Challenge (LD50) | Toxin | | |
|---|---|---|---|---|
| | | BoNT/A1 | BoNT/A2 | BoNT/$E_A$ |
| HCR/A1 | 10 | +, + | +, + | −, − |
| | 100 | +, +, +, + | +, +, +, + | −, − |
| | 1000 | +, + | +, + | −, − |
| | 100000 | +, +, +, + | +, +, +, + | −, − |
| HCR/E | 10 | −, − | −, − | +, + |
| | 100 | −, − | −, − | +, +, +, + |
| | 1000 | −, − | −, − | +, + |
| | 100000 | −, − | −, − | +, +, +, + |

[a]Mice were immunized with the indicated serotype of rHCR and then challenged by the indicated amount and serotype of BoNT. Mice were inspected for 96 hr and scored for survival (+) or death (−).

We claim:

1. A method of producing botulinum toxin C-terminal receptor binding domain (HCR), comprising the steps of
   (a) preparing *E. coli* transformed with an expression vector comprising DNA encoding at least 95% of the HCR protein,
   (b) inducing expression of the HCR protein at a reduced temperature in a culture media, wherein the reduced temperature is 16-18° C., and
   (c) purifying the HCR protein via extraction, wherein the extraction comprises a clarification by centrifugation and a filtration, wherein the purified HCR protein is at least 10 mg/L of culture medium.

2. The method of claim 1 wherein the protein is at least 15 mg/L of culture medium.

3. The method of claim 1 wherein the *E. coli* strain is *E. coli* BL-21 RIL.

4. The method of claim 1 wherein the expression vector is a pET expression vector resulting in an N-terminal $HIS_6$-HCR/A fusion protein.

5. The method of claim 1 wherein the purification of the HCR protein additionally comprises chromatography purification through nickel nitriloacetic acid (Ni-NTA) resin.

6. The method of claim 1 wherein the step (c) filtration is through a 0.2-2.0 μm filter.

7. The method of claim 1 wherein the purification of the HCR protein is in the presence of a reducing agent.

8. The method of claim 7 wherein the reducing agent is dithiothreitol (DTT).

9. The method of claim 1 wherein the HCR protein is selected from the group of the seven *C. botulinum* serotypes, serotypes A, B, C, D, E, F and G.

10. The method of claim 1 wherein the HCR protein is botulinum neurotoxin type A HCR protein.

11. The method of claim 1 where the culture is exposed to reduced temperature overnight.

12. The method of claim 1 wherein filtration is through a 0.2 μm-2 μm filter.

13. The method of claim 1 additionally comprising the step of exposing the HCR protein to an nitriloacetic acid (NTA) column.

* * * * *

UNITED STATES PATENT AND TRADEMARK OFFICE
CERTIFICATE OF CORRECTION

PATENT NO. : 7,820,411 B2  Page 1 of 1
APPLICATION NO. : 12/040542
DATED : October 26, 2010
INVENTOR(S) : Baldwin et al.

It is certified that error appears in the above-identified patent and that said Letters Patent is hereby corrected as shown below:

Column 1, lines 16-18 "This invention was made with United States government support awarded by the following agencies: NIH AI57153. The United States has certain rights in this invention." should be -- This invention was made with government support under grant number AI57153 awarded by the National Institutes of Health. The government has certain rights in the invention. --

Signed and Sealed this
Thirteenth Day of September, 2011

David J. Kappos
*Director of the United States Patent and Trademark Office*

SEQUENCE LISTING

```
<160> NUMBER OF SEQ ID NOS: 5

<210> SEQ ID NO 1
<211> LENGTH: 13
<212> TYPE: PRT
<213> ORGANISM: Artificial
<220> FEATURE:
<223> OTHER INFORMATION: Synthetic peptide.

<400> SEQUENCE: 1

Ile Thr Asn Asn Arg Leu Asn Asn Ser Lys Ile Tyr Ile
1               5                   10

<210> SEQ ID NO 2
<211> LENGTH: 13
<212> TYPE: PRT
<213> ORGANISM: Artificial
<220> FEATURE:
<223> OTHER INFORMATION: Synthetic peptide.

<400> SEQUENCE: 2

Ile Thr Asn Asn Arg Leu Thr Lys Ser Lys Ile Tyr Ile
1               5                   10

<210> SEQ ID NO 3
<211> LENGTH: 13
<212> TYPE: PRT
<213> ORGANISM: Artificial
<220> FEATURE:
<223> OTHER INFORMATION: Synthetic peptide.

<400> SEQUENCE: 3

Ile Thr Asn Asp Arg Leu Gly Asp Ser Lys Leu Tyr Ile
1               5                   10

<210> SEQ ID NO 4
<211> LENGTH: 13
<212> TYPE: PRT
<213> ORGANISM: Artificial
<220> FEATURE:
<223> OTHER INFORMATION: Synthetic peptide.

<400> SEQUENCE: 4
```

```
Phe Asp Lys Glu Leu Asn Glu Lys Glu Ile Lys Asp Leu
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic peptide.

<400> SEQUENCE: 5

Phe Asp Lys Glu Leu Asp Glu Thr Glu Ile Gln Thr Leu
1               5                   10
```